United States Patent
Duan et al.

(10) Patent No.: US 10,953,111 B2
(45) Date of Patent: Mar. 23, 2021

(54) CAPSULE FOR MEASURING MOTILITY OF A TARGET AREA

(71) Applicant: Ankon Medical Technologies (Shanghai) Co., LTD., Shanghai (CN)

(72) Inventors: Xiaodong Duan, Pleasanton, CA (US); Hongjiao Song, Dujiangyan (CN)

(73) Assignee: Ankon Medical Technologies (Shanghai) Co., LTD., Shanghai (CN)

( * ) Notice: Subject to any disclaimer, the term of this patent is extended or adjusted under 35 U.S.C. 154(b) by 389 days.

(21) Appl. No.: 15/881,679

(22) Filed: Jan. 26, 2018

(65) Prior Publication Data
US 2019/0030192 A1    Jan. 31, 2019

(30) Foreign Application Priority Data

Jul. 27, 2017  (CN) .......................... 201710622361.3

(51) Int. Cl.
*A61K 49/04*   (2006.01)
*A61K 9/48*    (2006.01)
(Continued)

(52) U.S. Cl.
CPC ............ *A61K 49/04* (2013.01); *A61B 5/4238* (2013.01); *A61B 5/4255* (2013.01);
(Continued)

(58) Field of Classification Search
CPC ..... A61B 5/6861; A61B 5/4255; A61B 90/39; A61B 5/4238; A61B 5/064;
(Continued)

(56) References Cited

U.S. PATENT DOCUMENTS

| | | | |
|---|---|---|---|
| 2006/0293581 A1* | 12/2006 | Plewes | ............... A61K 49/0419 600/407 |
| 2015/0202326 A1* | 7/2015 | Ohri | ....................... A61K 49/04 424/1.29 |
| 2018/0042563 A1* | 2/2018 | Kim | ....................... A61K 49/04 |

FOREIGN PATENT DOCUMENTS

| | | |
|---|---|---|
| CN | 10621519 A | 12/2016 |
| CN | 106492234 A | 3/2017 |
| RU | 2620162 C1 * | 5/2017 |

OTHER PUBLICATIONS

Y. Horikawa, H. Mieno, M. Inoue, G. Kajiyama. Gastrointestinal Motility in Patients with Irritable Bowel Syndrome Studied by Using Radiopaque Markers. 1999. Scandinavian Journal of Gastroenterology; 34:12,1190-1195 (Year: 1999).*

* cited by examiner

*Primary Examiner* — Jeffrey G Hoekstra
*Assistant Examiner* — Renee C Langhals
(74) *Attorney, Agent, or Firm* — Treasure IP Group, LLC

(57) ABSTRACT

A capsule for measuring motility of a target area is provided. An article of manufacture for measuring motility of a target area, comprises a first capsule and a second capsule. The first capsule comprises a first capsule enclosure; a first identification marker, having a weight of $W_{m1}$, wherein the first identification marker comprises a first visible element under X-ray, substantially circular shaped and having an outer diameter of A. The second capsule comprises a second capsule enclosure; a second identification marker, having a weight of $W_{m2}$, wherein the second identification marker comprises a second visible element under X-ray, substantially circular shaped and having an outer diameter of B. The first capsule enclosure and second capsule enclosure are substantially identical under all measurements in digestive behaviors; the weight of the first identification marker $W_{m1}$ (Continued)

and the weight of the second identification marker $W_{m2}$ differs less than 0.01 g; A is less than B.

15 Claims, 15 Drawing Sheets

(51) Int. Cl.
    *A61B 5/00*     (2006.01)
    *A61B 90/00*     (2016.01)
    *A61B 5/06*     (2006.01)

(52) U.S. Cl.
    CPC ............ *A61B 5/6861* (2013.01); *A61B 90/39* (2016.02); *A61K 9/48* (2013.01); *A61K 49/0409* (2013.01); *A61B 5/064* (2013.01); *A61B 2090/3966* (2016.02)

(58) Field of Classification Search
    CPC ...... A61B 2090/3966; A61B 2562/162; A61K 49/0414; A61K 49/04; A61K 49/0409; A61K 9/48; A61K 49/0404; A61K 47/6943; A61K 9/4808
    USPC ........................................................ 600/431
    See application file for complete search history.

CAPSULE FOR MEASURING MOTILITY OF A TARGET AREA

CROSS-REFERENCE OF RELATED APPLICATIONS

This application claims priority to Chinese Patent Application No. 201710622361.3 filed on Jul. 27, 2017, the contents of which are incorporated by reference herein.

FIELD OF INVENTION

The present invention generally relates to the field of gastrointestinal motility, and in particular to a capsule filled with identification markers for measuring motility of a target area.

BACKGROUND

Gastrointestinal tract is an important channel for digestion and absorption of human body, so to a large extent, whether its motility is normal or not may affect the human health. Gastrointestinal motility disorder is a common clinical disease in gastroenterology, plaguing a plurality of patients. Colonic motility dysfunction is the main cause of most functional colonic disorders, such as functional constipation, irritable bowel syndrome, etc., and is also a hot topic in the study of gastrointestinal motility. Colorectal transit time is an important indicator of the colonic motility, playing a significant role in determining the cause of disease, evaluating the severity of gastrointestinal motility dysfunction, guiding the selection of clinical treatment methods and assessing the efficacy of treatment.

A radiopaque marker capsule for gastrointestinal motility examination can measure the colorectal transit time. The radiopaque marker capsule comprises a capsule enclosure and a number of X-ray opaque markers filled in the capsule enclosure. The X-ray opaque markers are mostly made of medical grade plastics containing contrast agent, characterized by a variety of shapes, like a circle, a sphere, a rod and more. For existing X-ray opaque markers, however, if a number of markers pile up, it is hard to accurately identify the quantity of markers. Mostly, the quantity of markers is determined in an estimated manner, thereby affecting the accuracy of measurement results.

Therefore, an identification marker capsule that is highly identifiable is needed.

SUMMARY OF THE INVENTION

The present invention provides a capsule for detection of gastrointestinal motility, which implements detection by identification markers in the capsule.

In one embodiment of the present invention, an article of manufacture for measuring motility of a target area, comprises a first capsule and a second capsule. A first capsule comprises a first capsule enclosure; a first identification marker, having a weight of $W_{m1}$, wherein the first identification marker comprises a first visible element under X-ray, substantially circular shaped and having an outer diameter of A. The second capsule comprises a second capsule enclosure; a second identification marker, having a weight of $W_{m2}$, wherein the second identification marker comprises a second visible element under X-ray, substantially circular shaped and having an outer diameter of B. The first capsule enclosure and second capsule enclosure are substantially identical under all measurements in digestive behaviors; the weight of the first identification marker $W_{m1}$ and the weight of the second identification marker $W_{m2}$ differs less than 0.01 g; the outer diameter of the first visible element under X-ray (A) is less than the outer diameter of the second visible element under X-ray (B).

The article of manufacture for measuring motility of a target area further comprises a third capsule. The third capsule comprises a third capsule enclosure; a third identification marker, having a weight of $W_{m3}$, wherein the third identification marker comprises a third visible element under X-ray, substantially circular shaped and having an outer diameter of C, and the third identification marker has an outer diameter of $D_{m3}$, wherein A<B<C and C<$D_{m3}$, wherein 1.5≤B/A≤3, 1.5≤C/B≤3, B/A≥2, C/B≥2, or A:B:C=1:2:4.

The first capsule comprises x number of the first identification markers, and the second capsule comprises y number of the second identification markers, and x=y.

The first capsule comprises x number of the first identification markers, the second capsule comprises y number of the second identification markers, and the third capsule comprises z number of the third identification markers and x=y=z.

The third capsule enclosure of the third capsule is substantially identical to the first capsule enclosure and the second capsule enclosure under all measurements in digestive behaviors.

DETAILED DESCRIPTION

Figure 1:
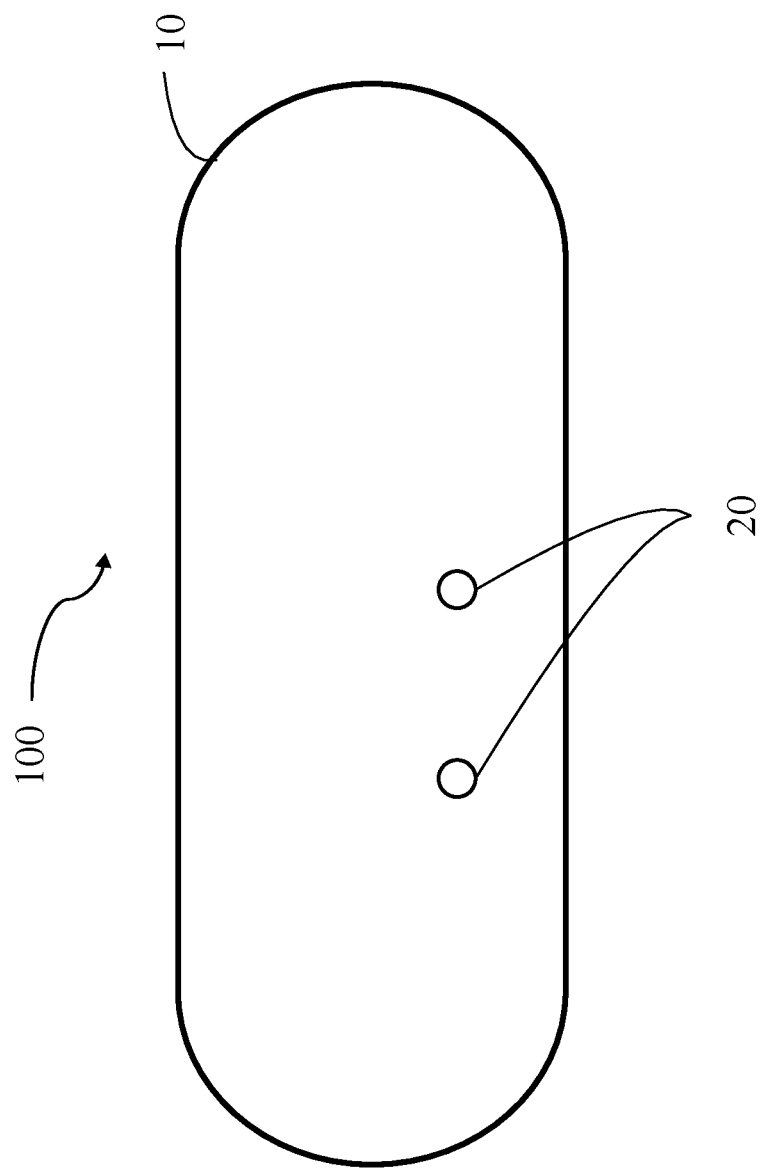
FIG. 1 is a schematic view of a capsule for measuring motility in a target area in accordance with a preferred embodiment of the present invention.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

The capsule for detection of gastrointestinal motility and its making method are described in detail below. Elements in the drawings are 100 Capsule for measuring the motility of a target area
10 Capsule enclosure
20 Identification marker FIG. 1 is a schematic view of a capsule for measuring motility in a target area in accordance with a preferred embodiment of the present invention. The capsule 100 for measuring the motility of a target area comprises the capsule enclosure 10 and a preset number of identification markers 20 filled in the capsule enclosure 10. FIG. 1 exemplifies a capsule enclosure 10 filled with 2 identification markers 20. The capsule 100 and identification markers 20 filled therein are used for measuring the motility of a target area, which can be the gastric, small intestinal or colonic areas. In one embodiment, the target area described herein can be the stomach, small intestine or colon in the gastrointestinal tract. In one embodiment, the target area described herein can be the in vitro stomach, small intestine or colon. In one embodiment, the target area described herein can be the stomach, small intestine or colon in the gastrointestinal tract model.

The capsule enclosure 10 is made of pharmaceutical gel or hypromellose with additives, food coloring as an example. The capsule enclosure 10 comprises gastric-dissolved capsule enclosure, enteric capsule enclosure or plant derived capsule enclosure. When the capsule enclosure 10 is a gastric-dissolved capsule enclosure or a plant derived capsule enclosure, the capsule enclosure 10 can be used for measuring the motility of stomach, small intestine and colon. When the capsule enclosure 10 is an enteric capsule, the capsule enclosure 10 can be used for measuring motility of small intestine and colon. The number of the identification marker 20 is preset in accordance with clinical efficacy, being any integer value in 15-25, such as 16, 18, 20, 22 or 24.

The identification marker 20 is used to simulate the movement of chyme in the target area, and measures the motility of the target area by examining quantity and location of residual markers therein. The identification marker 20 comprises a solid X-ray contrast agent, a medical grade plastic with a density less than 1.4 g/cm$^3$ and an auxiliary agent. The solid X-ray contrast agent comprises barium sulfate (BaSO4), bismuth salt and Tungsten. The bismuth salt comprises bismuth oxychloride, basic bismuth carbonate and bismuth oxide. The medical grade plastic comprises Polyvinyl chloride (PVC, 1.4 g/cm$^3$), Polystyrene (PS, 1.05 g/cm$^3$), Polyethylene (PE, 0.95 g/cm$^3$), Polypropylene (PP, 0.92 g/cm$^3$), Polycarbonate (PC, 1.18-1.22 g/cm$^3$), and Thermoplastic polyurethanes (TPU, 1.2 g/cm$^3$). The auxiliary agent comprises lubricants, plasticizers, heat stabilizers, and/or colorants.

The identification marker 20 is a circular, oval or spherical shaped marker. The circular or oval shaped identification marker 20 has a certain thickness that is larger than or equal to 0.5 mm Applicable thickness range is 0.5-1.0 mm, wherein the preferred thickness is 0.7-0.9 mm and the optimal thickness is 0.75 mm Outer diameter (O.D.) of the identification marker 20 is 4-6 mm, wherein the preferred O.D. is 4.4-4.7 mm and the optimal O.D. is 4.6 mm;

The identification marker 20 comprises a first element which can be visible and imaged under X-ray, a second element which cannot be imaged under X-ray and a third element which is a number of cavities. Weight of the first element is $W_1$, weight of the second element is $W_2$ and weight of the identification marker is $W_m=W_1+W_2$, wherein $0<W_1 \leq W_m$, $0 \leq W_2 < W_m$. The first element is made of a solid X-ray contrast agent, a first auxiliary agent and a first medical grade of plastic, and the first medical grade of plastic has a density less than 1.4 g/cm$^3$. The second element is made of a second auxiliary agent and a second medical grade of plastic, and the second medical grade of plastic has a density less than 1.4 g/cm$^3$. When there is a weight change in the first element or second element, the shape, number and/or sizes of the cavities are adjusted accordingly so that the weight of the identification marker 20 is at a target value. The target value is determined in accordance with the density range of the identification marker 20. In the preferred embodiment, the density range of the identification marker 20 is 1.0-1.7 g/cm$^3$.

In the preferred embodiment, the first medical grade plastic of the first element and the second medical grade plastic of the second element are the same or different. For example, both the first medical grade plastic and the second medical grade plastic are PVC, or the first medical grade plastic is PVC while the second medical grade plastic is TPU. The first auxiliary agent of the first element and the second medical grade plastic comprise the same or different components. For example, both the first medical grade plastic and the second medical grade plastic comprise lubricant, plasticizer, heat stabilizer and colorant, or the first medical grade plastic has colorant while the second medical grade plastic has not.

The thickness of the second element and the third element is the same as the thickness of the identification marker 20. The thickness of the first element is the same as the thickness of the identification marker 20, or different from (higher than or lower than) the thickness of the identification marker 20. When the thickness of the first element is different from the thickness of the identification marker 20, the absolute value of the difference is not more than 50% of the thickness of the identification marker 20. Hereinafter, the thickness of the first element will be the same as the thickness of the identification marker 20.

The cavities of the third element are not limited in shape, size, number and position. The cavities are optional in different shapes, such as oval, circular or square shaped cavities; the number of the cavities can be any integer value between 1-10; the position of the cavities can be anywhere around the first element; the size of each cavity is determined in accordance with the number of the cavities. In the preferred embodiment, the third element consists of even number of cavities and the cavities are symmetrically distributed around the first element.

The first element is used to identify the identification marker 20, ensuring a clear identification of the identification marker 20 viewed from different angles and directions. In the six views of the first element, at least two views of the first element are identical. The six views include front view, rear view, left view, right view, top view and bottom view.

In the preferred embodiment, when the identification marker 20 turns over in the target area, being viewed from any angle, the maximum lengths of the first element under X-ray are identical. The identification marker 20 turns over 360°. For example, when the first element has a cross section in a shape of a circle or a ring, if the identification marker 20 turns over 360° in the target area, being viewed from any angle, the maximum length of the first element under X-ray is the outer diameter of the first element; that is, the maximum length of the first element under X-ray is identical at any angle. When the first element has a cross section in a shape of a ring, the cross section of the first element is a ring having one or more cavities; to ensure X-ray imaging effect, absolute difference between outer diameter and inner diameter can be more than or equal to 0.5 mm In other embodiments, when the identification marker 20 turns over 360° in the target area, being viewed from any angle, the first element under X-ray has a maximum length. As viewed from two different angles, the first element may have different maximum lengths; the minimum value of the maximum length is more than or equal to 70% of the maximum value of the maximum length. For example, when the first element has a cross section in a shape of square, if the identification marker 20 turns over 360° in the target area, the maximum length of the first element under X-ray has a maximum value being the diagonal length of the square and has a minimum value being the side length of the square; so, the side length of the square is more than or equal to 70% of the diagonal length.

In the present invention, the identification marker 20 is clearly identifiable in the target area from different angles and directions, ensuring accurate identification of the quantity of markers even when they pile up in the target area, so as to improve the accuracy of measuring the motility of the target area.

In other embodiments, a identification marker 20 has a fourth element that can be imaged under X-ray, and a dimension of the fourth element is different from a dimension of the first element. The fourth element is used to replace the first element. Based on the different dimensions of the fourth element and the first element, the identification marker 20 that shows different dimensions under X-ray is formed. When the dimension of the fourth element is different from the dimension of the first element, the number, shape and/or sizes of the cavities of the third element is accordingly adjusted, so that the weight of the identification marker 20 is at the target value. The identification marker 20 having the fourth element and the identification marker 20 having the first element are the same in weight, or the absolute difference between their weights is less than 0.01 g.

In the preferred embodiment of the present invention, when the dimension of the fourth element is different from the dimension of the first element, the shape of the fourth element is identical to the shape of the first element, or the outer contour of the fourth element is identical to the outer contour of the first element. For example, when the fourth element and the first element are a square, the shape of the fourth element is identical to the shape of the first element; when the first element is a circle and the fourth element is a ring having more cavities, the outer contour of the first element is identical to the outer contour of the fourth element.

The fourth element and the first element are different in dimensions, producing a variety of the identification marker 20.

Three different identification markers 20 are described hereinafter as an example, and the outer contours of first elements of the three identification markers 20 imaged under X-rays are of the same shape. The three different identification markers 20 are described, with the first element being substantially circular shaped. The three identification markers 20 are a first identification marker, a second identification marker, and a third identification marker, respectively. In the preferred embodiment of the present invention, the first element is substantially a circular shaped, meaning that the first element has a cross section in a shape of a circle, or a ring having one or more cavities.

The first identification marker comprises a first element that can be imaged under X-ray. Cross section of the first imaged element is a circle, or a ring having one or more cavities. The first imaged element has an outer diameter of A, and the first identification marker has a weight of $W_{m1}$. The second identification marker comprises a second imaged element that can be imaged under X-ray. Cross section of the second imaged element is a circle, or a ring having one or more cavities. The second imaged element has an outer diameter of B, and the second identification marker has a weight of $W_{m2}$. Wherein, A<B; $W_{m1}=W_{m2}$, or absolute difference between $W_{m1}$ and $W_{m2}$ is less than 0.01 g.

The capsule 100 filled with the first identification markers is a first capsule. The first capsule further comprises a first capsule enclosure. The capsule 100 filled with the second identification markers is a second capsule. The second capsule further comprises a second capsule enclosure. The first capsule enclosure and the second capsule enclosure are substantially identical under all measurements in digestive behaviors. The identical measurements in digestive behaviors means that the first capsule enclosure and the second capsule enclosure are of the same type (e.g., both are gastric dissolved capsule enclosure) and are of equal weight.

The third identification marker comprises a third imaged element that can be imaged under X-ray. Cross section of the third imaged element is a circle, or a ring having one or more cavities. The third imaged element has an outer diameter of C, and the third identification marker has a weight of $W_{m3}$; wherein, outer diameter of the third identification marker is $D_{m3}$, A<B<C and C≤$D_{m3}$. $W_{m3}=W_{m1}$, or $W_{m3}=W_{m2}$; or absolute difference between $W_{m3}$ and $W_{m1}$ is less than 0.01 g, and the absolute difference between $W_{m3}$ and $W_{m2}$ is less than 0.01 g. The capsule 100 filled with the third identification markers is a third capsule. The third capsule further comprises a third capsule enclosure. The third capsule enclosure is substantially identical to the first capsule enclosure and the second capsule enclosure under all measurements in digestive behaviors.

The first imaged element, the second imaged element and the third imaged element have different outer diameters, so that the identification markers 20 are highly identifiable when viewed from any angle. In the embodiment, the ratio of outer diameters between the first imaged element and the second imaged element can be: 1.5≤B/A≤3 or B/A≥2; the ratio of outer diameters between the second imaged element and the third imaged element can be: 1.5≤C/B≤3 or C/B≤2. The ratio of outer diameters between the first imaged element, the second imaged element and the third imaged element can be: 1.5≤B/A≤3 and 1.5≤C/B≤3; or B/A≥2 and C/B≥2. In the preferred embodiment of the present invention, A:B:C=1:2:4 is preferred.

In other embodiment, the ratio of outer diameters between the first imaged element and the second imaged element can be: 1≤B/A≤3 or B/A≥1; the ratio of outer diameters between the second imaged element and the third imaged element can be: 1≤C/B≤3 or C/B≤1. The ratio of outer diameters between the first imaged element, the second imaged element and the third imaged element can be: 1≤B/A≤3 and 1≤C/B≤3; or B/A≥1 and C/B≥1. In the preferred embodiment of the present invention, A:B:C=2:3:4 is preferred.

When the first imaged element, the second imaged element and the third imaged element are different in outer diameters, the shape, sizes and/or number of the cavities of the first identification marker, the second identification marker and the third identification marker are adjusted to make the weight of first identification marker $W_{m1}$, the weight of the second identification marker $W_{m2}$ and the weight of the third identification marker $W_{m3}$ meet the requirements set forth hereinabove, for example, $W_{m1}=W_{m2}=W_{m3}$.

Figure 2:
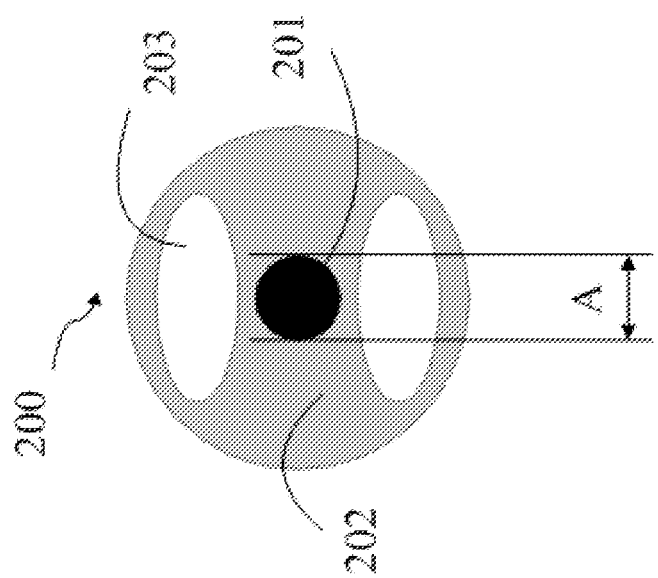
FIG. 2 is an illustration of a top view of a first exemplar identification marker in accordance with the first embodiment of the present invention.
Figure 3:
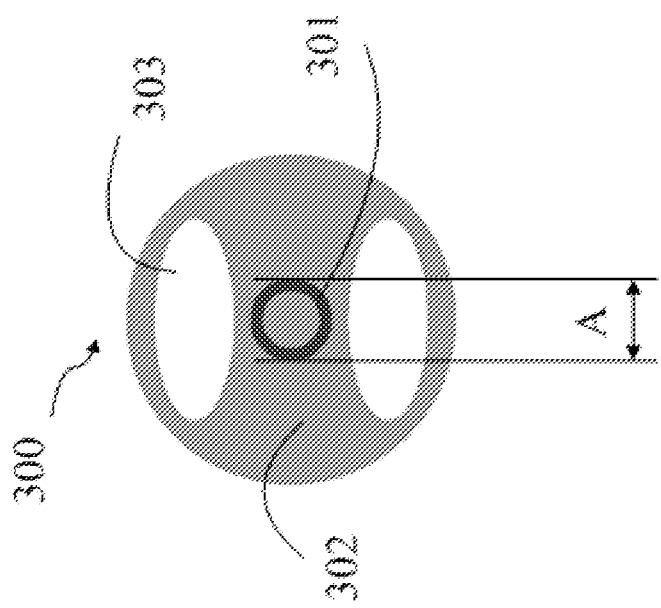
FIG. 3 is an illustration of a top view of a second exemplar identification marker in accordance with the first embodiment of the present invention.
Figure 4:
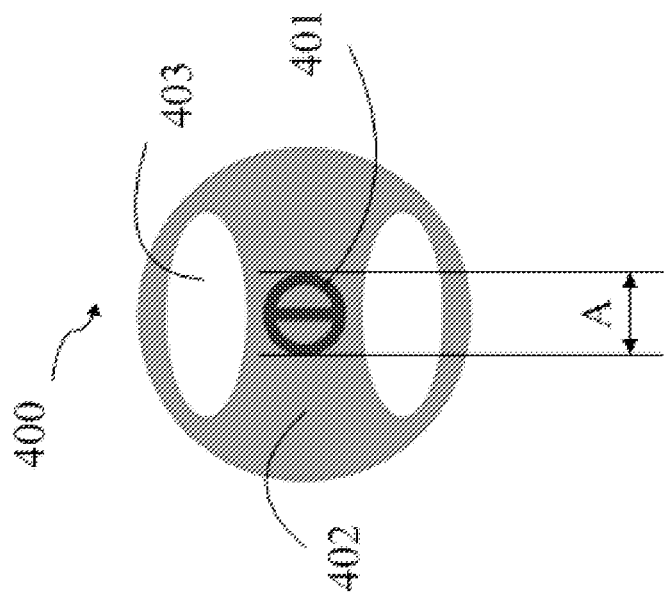
FIG. 4 is an illustration of a top view of a third exemplar identification marker in accordance with the first embodiment of the present invention.
Figure 5:
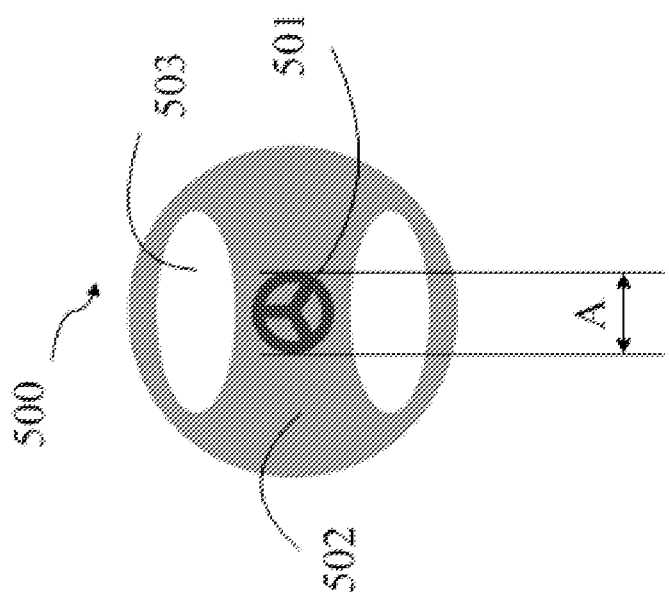
FIG. 5 is an illustration of a top view of a fourth exemplar identification marker in accordance with the first embodiment of the present invention.
Figure 6:
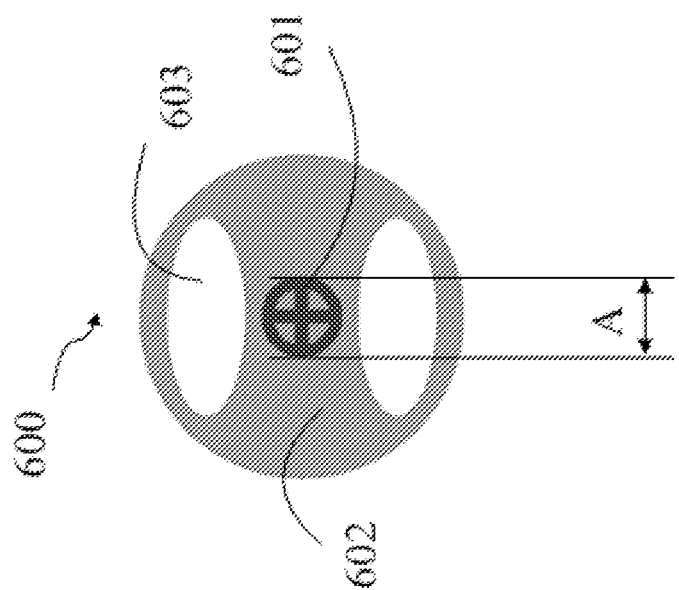
FIG. 6 is an illustration of a top view of a fifth exemplar identification marker in accordance with the first embodiment of the present invention.

The FIGS. 2~6, illustrate a cross section of the first identification marker. As shown in the FIGS. 2~6, the first identification marker has a cross section in a shape of a circle, being composed of a first imaged element, a second element and a third element. The first imaged element is the black area as shown in the FIGS. 2~6, which is a circle or a ring having one or more cavities; the first imaged element in the FIG. 2 is a circle, the first imaged element in the FIG. 3 is a ring having one cavity, the first imaged element in the FIGS. 4~6 is a ring having a plurality of cavities. The second element is the grey area as shown in the FIGS. 2~6, and the third element is the white area as shown in the FIGS. 2~6. The white area comprises 2 oval shaped cavities which are symmetrically distributed at the upper and lower positions of the first imaged element. The position of the first imaged element is just an example, which can be located not only at the center of the first identification marker, but also at any position around the center that is not the third element, e.g. slightly upward, downward, leftward and rightward. The number, position, shape and sizes of the cavities are only an example. The number allows for modification in accordance with actual situations, including 3, 4, etc. for example. The third element can be located anywhere around the first element, with the shape modifiable to be a circle, a square and others, and the size settable in accordance with the number of cavities and the shape of the first imaged element, so as to make the weight of the first identification marker $W_{m1}$ as shown in FIGS. 2~6 equal to the weight of the second identification marker $W_{m2}$ and the weight of the third identification marker $W_{m3}$.

Figure 7:
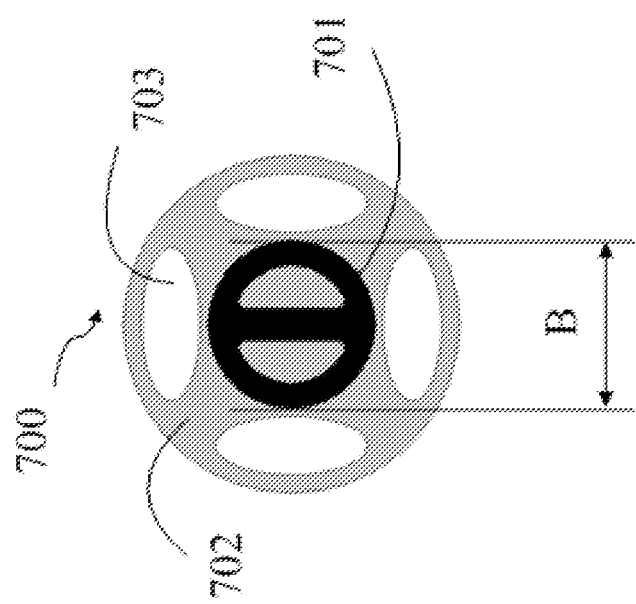
FIG. 7 is an illustration of a top view of a first exemplar identification marker in accordance with the second embodiment of the present invention.
Figure 8:
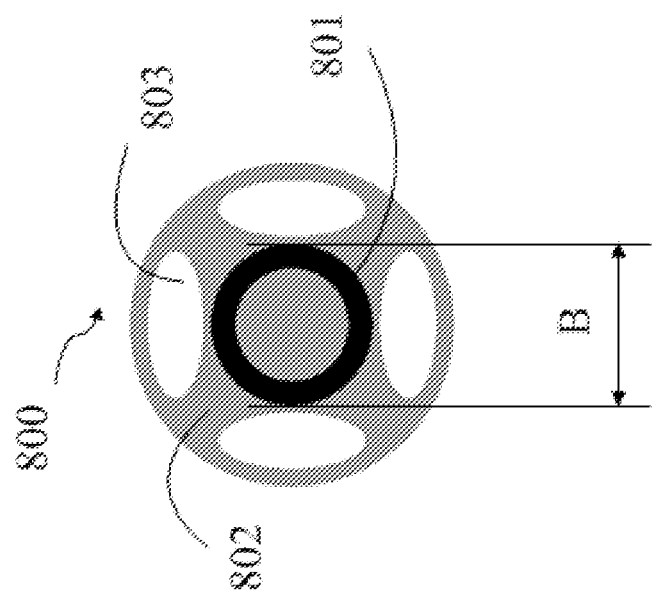
FIG. 8 is an illustration of a top view of a second exemplar identification marker in accordance with the second embodiment of the present invention.
Figure 9:
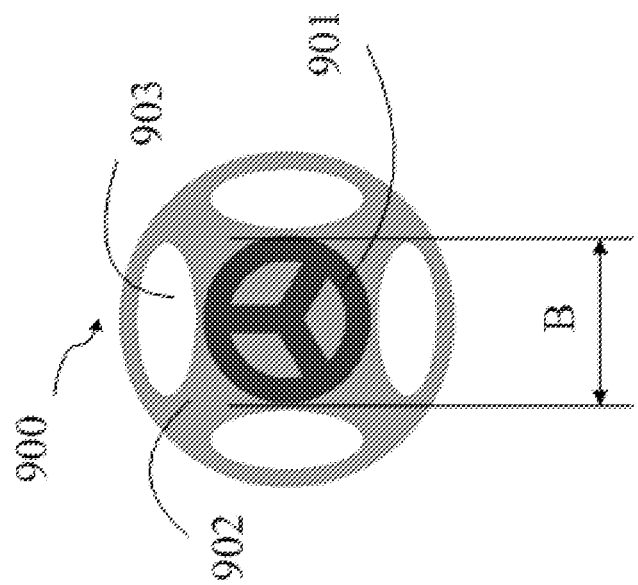
FIG. 9 is an illustration of a top view of a third exemplar identification marker in accordance with the second embodiment of the present invention.
Figure 10:
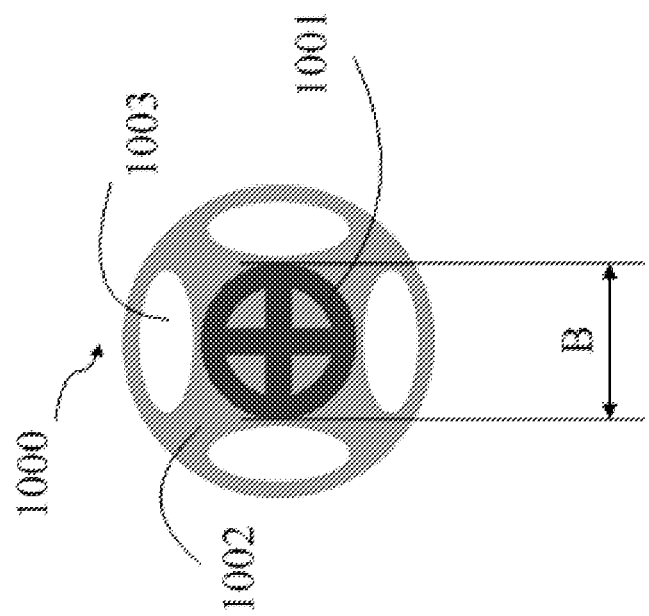
FIG. 10 is an illustration of a top view of a fourth exemplar identification marker in accordance with the second embodiment of the present invention.

The FIGS. 7~10, illustrate a cross section of the second identification marker. As shown in the FIGS. 7~10, the second identification marker has a cross section in a shape of a circle, being composed of a second imaged element, a second element and a third element. The second imaged element is the black area as shown in the FIGS. 7~10, which is a circle or a ring having one or more cavities; although there is not a illustration of the second imaged element having a shape of a circle in the FIGS. 7~10, it does not mean that the second imaged element cannot be made into a circle; the second imaged element in the FIG. 8 is a ring having one cavity, and the second imaged element in the FIGS. 7, 9 and 10 is a ring having more cavities. The second element is the grey area as shown in the FIGS. 7~10, and the third element is the white area as shown in the FIGS. 7~10. The white area comprises 4 oval shaped cavities which are symmetrically distributed at the upper, lower, left and right positions of the second image element. The position of the second image element is just an example, which can be located not only at the center of the second identification marker, but also at any position around the center that is not the third element, e.g. slightly upward, downward, leftward and rightward. The number, position, shape and sizes of the cavities are only an example. The number allows for modification in accordance with actual situations, including 2, 3, 5, 6 etc. for example. The third element can be located anywhere around the second imaged element, with the shape modifiable to be a circle, a square and others, and the size settable in accordance with the number of cavities and the shape of the second imaged element, so as to make the weight of the second identification marker $W_{m2}$ as shown in FIGS. 7~10 equal to the weight of the first identification marker $W_{m1}$ and the weight of the third identification marker $W_{m3}$.

Figure 11:
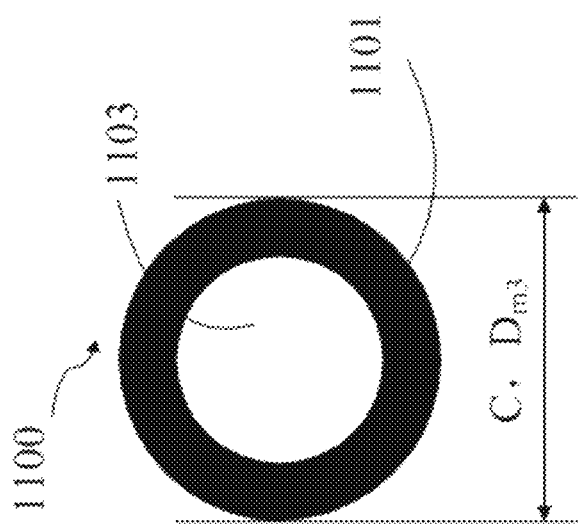
FIG. 11 is an illustration of a top view of a first exemplar identification marker in accordance with the third embodiment of the present invention.
Figure 12:
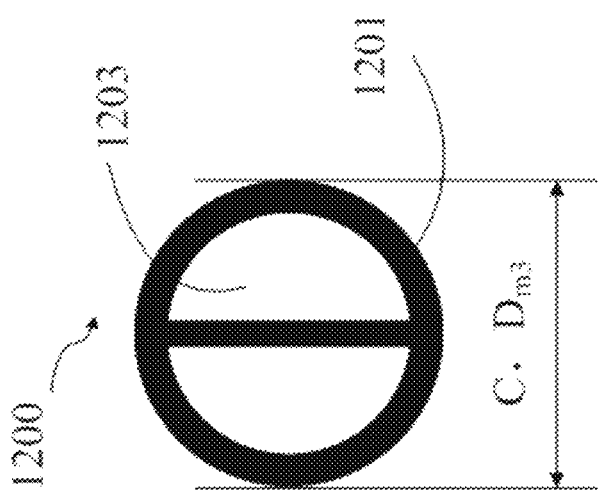
FIG. 12 is an illustration of a top view of a second exemplar identification marker in accordance with the third embodiment of the present invention.
Figure 13:
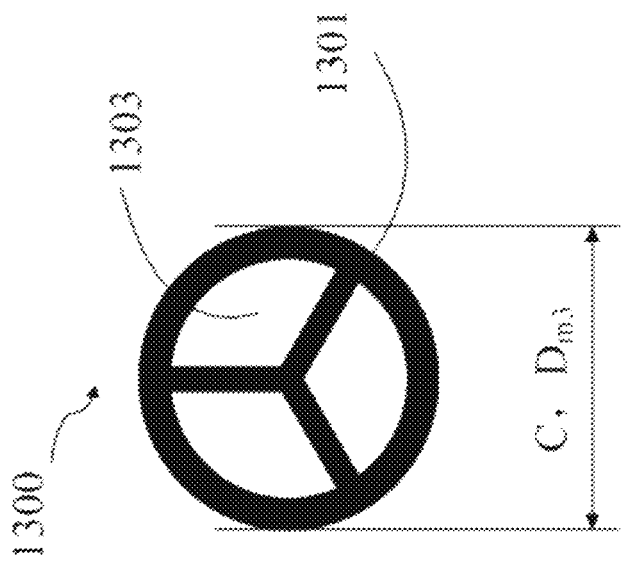
FIG. 13 is an illustration of a top view of a third exemplar identification marker in accordance with the third embodiment of the present invention.
Figure 14:
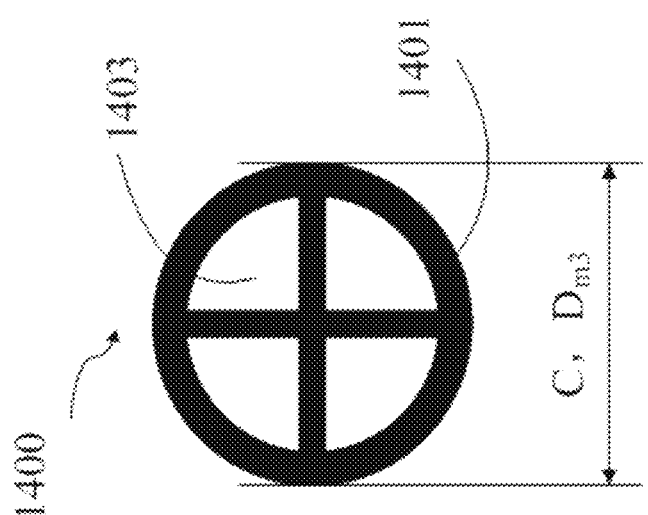
FIG. 14 is an illustration of a top view of a fourth exemplar identification marker in accordance with the third embodiment of the present invention.

The FIGS. 11~14, illustrate a cross section of the third identification marker. As shown in the FIGS. 11~14, the third identification marker has a cross section in a shape of a circle, being composed of the third imaged element and the third element. The third imaged element is the black area as shown in the FIGS. 11~14, which is a ring having one or more cavities; the third imaged element in the FIG. 11 is a ring having one cavity, and the third imaged element in the FIG. 12~14 is a ring having a plurality of cavities. The third element is the white area as shown in the FIGS. 11~14. Ratio of dimensions between the third imaged element and the third element can be adjusted to make the weight of the third identification marker $W_{m3}$ as shown in the FIGS. 11~14 equal to the weight of the first identification marker $W_{m1}$ and the weight of the second identification marker $W_{m2}$. In other embodiments, the outer diameter of the third imaged element can be less than the outer diameter of the third identification marker; in this case, the area between the outer diameter of the third imaged element and the outer diameter of the third identification marker is the second element which can also be filled with the third element having a certain number of cavities.

The number, shape and/or sizes of the cavities of the third element are adjustable to make the weights of the first, the second and the third identification markers consistent, and the density of the three identification markers 20 as close as possible to the density of chyme in the gastrointestinal tract, so as to achieve a better simulation effect. In the preferred embodiment of the present invention, the density of the identification marker 20 is set to be between 1.0-1.7 g/cm³ in accordance with the density of the chyme in the gastrointestinal tract of about 1.09 g/cm³. That is, the density of the three identification markers 20 is between 1.0-1.7 g/cm³.

Figure 15:
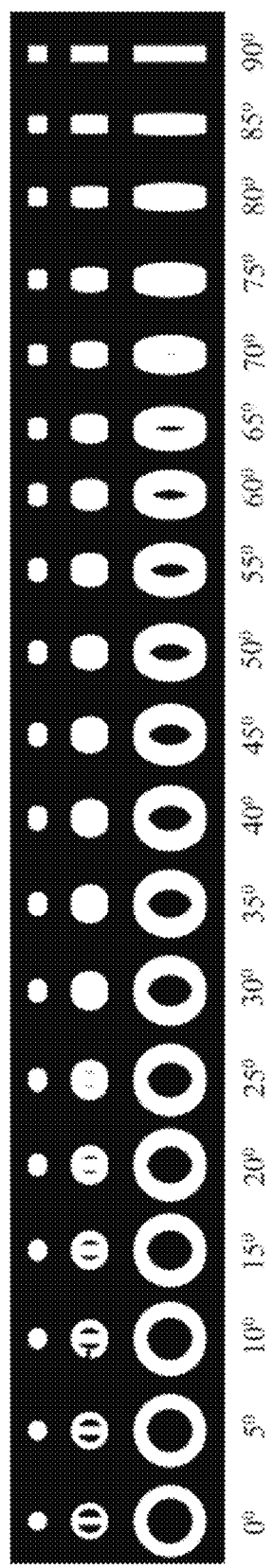
FIG. 15 is an illustration of an imaging effect of different exemplar identification markers at different turning angles.

The FIG. 15 illustrates an imaging effect of different exemplar identification markers 20 at different turning angles.

In accordance with the FIG. 15, the imaging effects of a first identification marker as shown in FIG. 2, a second identification marker as shown in FIG. 7 and a third identification marker as shown in FIG. 11 at a turning angle of 0-90° are clearly illustrated therein. Based on the imaging effects shown in the FIG. 15, the three identification markers 20 can be clearly identified at different angles; even when a number of different identification markers 20 pile up, the residual quantity of the identification markers 20 in the gastrointestinal tract can be clearly identified.

The capsule 100 is used for measuring the motility of stomach, small intestine and colon. Measuring methods of the colonic motility comprises simple measuring and segmented measuring. For specific measuring method, refer to Chinese Patent Application No. 201610601158.3. For measuring of gastric motility and small intestinal motility, a capsule 100 is enough; for simple measuring of colonic motility, a capsule 100 is used or two capsules 100 are used at an interval; for segmented measuring of colonic motility, three capsules 100 are used continuously.

When a capsule 100 is used for motility measuring, the identification markers 20 placed inside the capsule enclosure in a predetermined number are the same or different. That is, the capsule 100 comprises a predetermined number of same identification markers 20, for example, a capsule 100 containing 24 first identification markers 20; or a capsule 100 containing different identification markers 20, and the total number of the different markers is the predetermined number.

In the preferred embodiment of the present invention, the first identification marker, the second identification marker and the third identification marker are used to describe that the capsule 100 contains different identification marker 20. In one example, the capsule 100 contains x number of first identification markers and y number of second identification markers, wherein x+y=the predetermined quantity. When the predetermined quantity is an even number, the quantity of the identification marker 20 can be set as x=y. In another example, the capsule 100 contains y number of second identification markers and z number of third identification markers, wherein y+z=the predetermined quantity. When the predetermined quantity is an even number, the quantity of the identification marker 20 can be set as y=z. In another example, the capsule 100 contains x number of first identification markers and z number of third identification markers, wherein x+z=the predetermined quantity. When the predetermined quantity is an even number, the quantity of the identification marker 20 can be set as y=z. In another example, the capsule 100 contains x number of first identification markers, y number of second identification markers and z number of third identification markers, wherein x+y+z=the predetermined quantity. When the predetermined quantity is a multiple of 3, the quantity of the identification marker 20 can be set as x=y=z.

In the case of continuous use of a plurality of capsules 100 for gastrointestinal motility measuring, each of the capsules 100 contains a predetermined number of identical markers while the identification markers 20 are different in different capsules 100. In one example, when it is necessary to continuously use three capsules 100, the three capsules are respectively: capsule 100 containing a predetermined number of the first identification markers, capsule 100 containing a predetermined number of the second identification markers, and capsule 100 containing a predetermined number of the third identification markers.

When the identification markers 20 in the capsule 100 are different, and at different angles, the maximum length of the first element of the identification markers 20 under X-ray is identical, the maximum length is the outer diameter of the first element; the ratio of outer diameters between the first element of different identification markers 20, e.g. the outer diameter ratio between the first imaged element, the second imaged element and the third imaged element, shows as above, is no longer repeated herein.

When the capsule 100 contains different identification markers 20, and at different angles, the minimum value of the maximum length of the first element of the identification marker 20 under X-ray is more than or equal to 70% of the maximum value of the maximum length of the first element, provided there are three different identification markers 20 and the maximum lengths of the first element have three maximum values of E, F and G, E<F<G and G≤$Dm_3$. In one embodiment, the ratio between E and F can be: 1.5≤F/E≤3 or F/E≥2; the ratio between F and G can be 1.5≤G/F≤3 or G/F≥2; the ratio between E, F and G can be 1.5≤F/E≤3, and 1.5≤G/F≤3; or F/E≥2, and G/F≥2. In the preferred embodiment, E:F:G=1:2:4 is preferred. In other embodiment, the ratio between E and F can be: 1≤F/E≤3 or F/E≥1; the ratio between F and G can be 1≤G/F≤3 or G/F≥1; the ratio between E, F and G can be 1≤F/E≤3, and 1≤G/F≤3; or F/E≥1, and G/F≥1. In the preferred embodiment, E:F:G=2:3:4 is preferred.

In the preferred embodiment of the present invention, the different identification markers 20 can be clearly identified at various angles; even if the different markers 20 pile up, the quantity thereof can be clearly identified; this prevents failure to determine the residual quantity of the identification markers 20 in the gastrointestinal tract resulted from excessive quantity of the identification markers 20 placed inside the target area, and enables a clear identification of the residual quantity of the identification markers 20, so as to improve the accuracy of measuring the motility of the target area.

In preparation of the identification marker 20, a mold is first prepared according to a shape of the identification marker 20; then a first pre-prepared mixture of solid X-ray contrast agent, the first auxiliary agent and the first medical grade plastic is added to a first area of the mold, and a second pre-prepared mixture of the second auxiliary agent and the second medical grade plastic is added to a second area of the mold; further, the identification marker 20 is made through injection molding or extrusion process. After cleaning and disinfection, a predetermined number of the identification marker 20 is filled into the capsule enclosure 10, and packed and disinfected to form the capsule 100.

When the identification marker 20 is prepared using an injection molding or extrusion process, and the solid X-ray contrast agent is dispersed evenly in the first pre-prepared mixture of the medical grade plastic and auxiliary agent, the identification marker 20 is clearly imaged as a first element under the X-ray.

According to the present invention, when the capsule 100 is used for measuring the motility of a target area, only once or twice plain abdominal X-ray examination can lead to an accurate determination of the colon transit function, which effectively reduce the use of X-ray radiation and thereby reduce damage to user's body due to exposure to radiation.

According to the present invention, when a continuous use of the capsule 100 is needed, different capsules 100 contain different identification markers 20 which however come with the same weight, and thereby effectively reduce deviation of measuring results caused by difference of the identification markers 20. In addition, each of the identification markers 20 can be clearly identified at various angles, and the residual quantity of identification markers 20 can be accurately identified even if there is a pileup of markers, thus effectively improving the accuracy of motility measuring.

The element list is attached below.

200 first exemplar identification marker of the first embodiment;

201 a first element, which can be visible and imaged under X-ray, having a weight of $W_1$;
202 a second element, which cannot be imaged under X-ray, having a weight of $W_2$;
203 a third element, which contains a number of cavities;
300 second exemplar identification marker of the first embodiment;
301 a first element, which can be visible and imaged under X-ray, having a weight of $W_1$;
302 a second element, which cannot be imaged under X-ray, having a weight of $W_2$;
303 a third element, which contains a number of cavities;
400 third exemplar identification marker of the first embodiment;
401 a first element, which can be visible and imaged under X-ray, having a weight of $W_1$;
402 a second element, which cannot be imaged under X-ray, having a weight of $W_2$;
403 a third element, which contains a number of cavities;
500 fourth exemplar identification marker of the first embodiment;
501 a first element, which can be visible and imaged under X-ray, having a weight of $W_1$;
502 a second element, which cannot be imaged under X-ray, having a weight of $W_2$;
503 a third element, which contains a number of cavities;
600 fifth exemplar identification marker of the first embodiment;
601 a first element, which can be visible and imaged under X-ray, having a weight of $W_1$;
602 a second element, which cannot be imaged under X-ray, having a weight of $W_2$;
603 a third element, which contains a number of cavities;
700 first exemplar identification marker of the second embodiment;
701 a first element, which can be visible and imaged under X-ray, having a weight of $W_1$;
702 a second element, which cannot be imaged under X-ray, having a weight of $W_2$;
703 a third element, which contains a number of cavities;
800 second exemplar identification marker of the second embodiment;
801 a first element, which can be visible and imaged under X-ray, having a weight of $W_1$;
802 a second element, which cannot be imaged under X-ray, having a weight of $W_2$;
803 a third element, which contains a number of cavities;
900 third exemplar identification marker of the second embodiment;
901 a first element, which can be visible and imaged under X-ray, having a weight of $W_1$;
902 a second element, which cannot be imaged under X-ray, having a weight of $W_2$;
903 a third element, which contains a number of cavities;
1000 fourth exemplar identification marker of the second embodiment;
1001 a first element, which can be visible and imaged under X-ray, having a weight of $W_1$;
1002 a second element, which cannot be imaged under X-ray, having a weight of $W_2$;
1003 a third element, which contains a number of cavities;
1100 a first exemplar identification marker of the third embodiment;
1101 a first element, which can be visible and imaged under X-ray, having a weight of $W_1$;
1103 a third element, which contains a number of cavities;
1200 a second exemplar identification marker of the third embodiment;
1201 a first element, which can be visible and imaged under X-ray, having a weight of $W_1$;
1203 a third element, which contains a number of cavities;
1300 a third exemplar identification marker of the third embodiment;
1301 a first element, which can be visible and imaged under X-ray, having a weight of $W_1$;
1303 a third element, which contains a number of cavities;
1400 a fourth exemplar identification marker of the third embodiment;
1401 a first element, which can be visible and imaged under X-ray, having a weight of $W_1$;
1402 a second element, which cannot be imaged under X-ray, having a weight of $W_2$;
1403 a third element, which contains a number of cavities.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in particular the matters of shape, size and arrangement of parts within the principles of the present disclosure, up to and including the full extent established by the broad general meaning of the terms used in the claims.

What is claimed is:

1. An article of manufacture for measuring motility of a target area, comprising
    a first capsule, comprises
        a first capsule enclosure;
        a first identification marker, having a weight of Wmi, wherein the first identification marker comprises a first visible element under X-ray, circular shaped and having an outer diameter of A;
    a second capsule, comprises
        a second capsule enclosure;
        a second identification marker, having a weight of Wm2, wherein the second identification marker comprises a second visible element under X-ray, circular shaped and having an outer diameter of B;
    wherein
        the first capsule enclosure and second capsule enclosure are identical under all measurements in digestive behaviors;
        the weight of the first identification marker Wmi and the weight of the second identification marker Wm2 differs less than 0.01 g;
        the outer diameter of the first visible element under X-ray (A) is less than the outer diameter of the second visible element under X-ray (B) and outer diameter of the first identification marker and outer diameter of the second identification marker is are identical but the outer diameters of the first and second visible elements are different, wherein the visible element and second visible element have a same material composition;
        the motility of the target area is configured to be measured by a single X-ray radiation.

2. The article of manufacture for measuring motility of a target area of claim 1, further comprises
    a third capsule, comprises
        a third capsule enclosure;
        a third identification marker, having a weight of Wm3, wherein the third identification marker comprises a third visible element under X-ray, circular shaped and having an outer diameter of C and the third identification marker has an outer diameter of Dm3, wherein A<B<C and C=<$D_{m3}$.

3. The article of manufacture for measuring motility of a target area of claim 1, wherein 1.5≤B/A≤3.

4. The article of manufacture for measuring motility of a target area of claim 2, wherein 1.5≤C/B≤3.

5. The article of manufacture for measuring motility of a target area of claim 1, wherein B/A≥2.

6. The article of manufacture for measuring motility of a target area of claim 2, wherein C/B≥2.

7. The article of manufacture for measuring motility of a target area of claim 2, wherein A:B:C 1:2:4.

8. The article of manufacture for measuring motility of a target area of claim 2, wherein the first capsule comprises x number of the first identification markers, and the second capsule comprises y number of the second identification markers, and x=y.

9. The article of manufacture for measuring motility of a target area of claim 2, wherein the first capsule comprises x number of the first identification markers, the second capsule comprises y number of the second identification markers, and the third capsule comprises z number of the third identification markers and x=y=z.

10. The article of manufacture for measuring motility of a target area of claim 2, wherein the third capsule enclosure of the third capsule is identical to the first capsule enclosure and the second capsule enclosure under all measurements in digestive behaviors.

11. The article of manufacture for measuring motility of a target area of claim 1, wherein 1≤B/A≤3.

12. The article of manufacture for measuring motility claim 8, wherein 1≤C/B≤3.

13. The article of manufacture for measuring motility claim 1, wherein B/A≥1.

14. The article of manufacture for measuring motility claim 8, wherein C/B≥1.

15. The article of manufacture for measuring motility claim 8, wherein A:B:C=2:3:4.

* * * * *